(12) United States Patent
Amoyal et al.

(10) Patent No.: US 12,315,612 B2
(45) Date of Patent: May 27, 2025

(54) TAMPER-RESISTANT CONTAINER WITH UNIQUE IDENTITY AUTHENTICATION AND NETWORK-ENABLED SECURITY FEATURES

(71) Applicant: Impruvon, Inc., King George, VA (US)

(72) Inventors: Justin Michael Amoyal, Ashburn, VA (US); Michael Jared Mazzocco, King George, VA (US)

(73) Assignee: Impruvon, Inc., King George, VA (US)

( * ) Notice: Subject to any disclaimer, the term of this patent is extended or adjusted under 35 U.S.C. 154(b) by 117 days.

(21) Appl. No.: 17/496,538

(22) Filed: Oct. 7, 2021

(65) Prior Publication Data
US 2022/0028515 A1    Jan. 27, 2022

Related U.S. Application Data

(63) Continuation-in-part of application No. 16/923,641, filed on Jul. 8, 2020, now Pat. No. 11,166,879.

(60) Provisional application No. 62/871,426, filed on Jul. 8, 2019.

(51) Int. Cl.
*G16H 20/13* (2018.01)
*G06F 21/31* (2013.01)

(52) U.S. Cl.
CPC ............. *G16H 20/13* (2018.01); *G06F 21/31* (2013.01)

(58) Field of Classification Search
CPC ......... G16H 20/13; G16H 40/67; G06F 21/31
See application file for complete search history.

(56) References Cited

U.S. PATENT DOCUMENTS

| | | |
|---|---|---|
| 5,119,969 A | 6/1992 | Haber |
| 5,478,586 A | 12/1995 | Connor |
| 5,921,433 A | 7/1999 | Friar et al. |
| 5,957,358 A * | 9/1999 | Getz .................. B65H 35/0006 |
| | | 206/820 |
| D424,850 S | 5/2000 | Handfield et al. |
| 6,422,133 B1 | 7/2002 | Brady |
| (Continued) | | |

*Primary Examiner* — Michael Collins
(74) *Attorney, Agent, or Firm* — Offit Kurman; Tod A. Kupstas

(57) ABSTRACT

The present invention is that of a secure dispensing systems and methods for prescription medications. In certain embodiments, the system comprises a dispenser with a unique user identity authentication sensor, such as a fingerprint scanner, in combination with a vibration sensor to detect movement. The user identity authentication and vibration sensors communicate with a provided computer software application via application program interface such as may be installed on a smartphone. Certain embodiments also allow for improved compliance with prescription instructions by rewarding users for prescription compliance by providing audiovisual and gaming rewards. Dispensers according to the invention may be manual or automated in nature and may be remotely activated using modern computing and networking technologies, and may also communicate through telehealth networks for automated prescription refills. The methods disclosed herein provide secure access to medications, tamper prevention improved compliance, telehealth system compatibility, and improved medication independence for persons in need.

3 Claims, 11 Drawing Sheets

(56) References Cited

U.S. PATENT DOCUMENTS

| | | |
|---|---|---|
| 6,797,304 B2 | 9/2004 | McGonagle |
| 6,834,775 B1 | 12/2004 | Collins |
| 6,848,593 B2* | 2/2005 | Papp .................. G06V 20/66 |
| | | 221/25 |
| 7,040,218 B1 | 5/2006 | Biolchini, Jr. |
| 7,194,951 B1 | 3/2007 | Porter |
| 7,917,246 B2 | 3/2011 | Handfield et al. |
| 7,963,201 B2 | 6/2011 | Wallace et al. |
| 8,499,965 B2* | 8/2013 | Sheffield ............ B65H 37/005 |
| | | 221/45 |
| 8,517,214 B2* | 8/2013 | Lowry .................... A47F 3/04 |
| | | 221/124 |
| 8,600,548 B2 | 12/2013 | Bossi et al. |
| D773,175 S | 12/2016 | Fagen |
| 9,579,264 B1 | 2/2017 | Litton |
| 10,327,995 B2 | 6/2019 | Wang et al. |
| 10,343,806 B2 | 7/2019 | Fagen et al. |
| D904,007 S | 12/2020 | Lavin et al. |
| D942,771 S | 2/2022 | Loiseau |
| 11,348,399 B1 | 5/2022 | Sanso et al. |
| 11,410,764 B1 | 8/2022 | Rosomoff et al. |
| D964,017 S | 9/2022 | Minocha et al. |
| 11,554,081 B1 | 1/2023 | Gellman |
| 11,617,436 B1 | 4/2023 | McNannay et al. |
| 11,743,424 B1 | 8/2023 | Lavin et al. |
| 2005/0061825 A1 | 3/2005 | Willoughby |
| 2005/0281706 A1 | 12/2005 | Funke et al. |
| 2006/0058918 A1 | 3/2006 | Handfield et al. |
| 2007/0289987 A1* | 12/2007 | Tramontina ............ A47K 5/12 |
| | | 221/96 |
| 2008/0035520 A1 | 2/2008 | Caracciolo et al. |
| 2010/0298975 A1* | 11/2010 | Heath .................... G16H 20/10 |
| | | 700/244 |
| 2011/0193716 A1 | 8/2011 | Goff et al. |
| 2015/0014261 A1* | 1/2015 | Johnson .............. A47F 7/0007 |
| | | 211/59.2 |
| 2016/0324727 A1* | 11/2016 | Waugh ................. G16H 20/13 |
| 2017/0197748 A1 | 7/2017 | Fagen et al. |
| 2017/0197775 A1 | 7/2017 | Fagen et al. |
| 2018/0104153 A1 | 4/2018 | Wang et al. |
| 2018/0177683 A1 | 6/2018 | Wjngaarden et al. |
| 2018/0243170 A1* | 8/2018 | Mahal ..................... A61J 7/04 |
| 2018/0303719 A1* | 10/2018 | DeLury ................... A61J 1/03 |
| 2019/0392934 A1* | 12/2019 | Tabakin ................ G16H 10/60 |
| 2020/0323738 A1 | 10/2020 | Bear et al. |
| 2021/0130076 A1 | 5/2021 | Brinckerhoff |
| 2022/0096330 A1 | 3/2022 | Rivard |
| 2022/0105008 A1 | 4/2022 | Long |
| 2022/0312961 A1 | 10/2022 | Rahilly et al. |
| 2022/0313558 A1 | 10/2022 | Duda |
| 2023/0000724 A1 | 1/2023 | Pruyn |

\* cited by examiner

| Health Improvement | |
|---|---|
| Caregivers | Organization was successfully updated |
| Individuals Medicines SLOadmins SLOs Simpills | Edit Organization  Delete Organization <br><br>SLO Details<br>Name    GMU Supported Living Otg. 1<br><br>Individuals  Caregivers  SLO Admins<br><br>| Email | Phone | Name1 | Name2 | Created At | New Patient |<br>|---|---|---|---|---|---|<br>| js@y.com | 5551111 | John | Smith | May 05 2021 | View |<br>| lr@g.com | 5552222 | Lara | Reed | May 06 2021 | View |<br>| ds@m.com | 5553333 | Dave | Son | May 07 2021 | View | |

FIG. 7A

| Health Improvement | |
|---|---|
| Caregivers Individuals Medicines SLOadmins SLOs Simpills | Details<br>Email<br>Phone<br>First Name<br>Last Name<br>Organization  COMPANY<br>Add Caregivers<br>*Please enter the name or phone number of the caregiver*<br><br>Doses<br>Add New Dose<br><br>Create User  Cancel |

FIG. 7B

| Health Improvement | | |
|---|---|---|
| Caregivers Individuals Medicines SLOadmins SLOs Simpills | Individual Details | |
| | Email | js@y.com |
| | Phone | 5551111 |
| | First Name | John |
| | Last Name | Smith |
| | Role | patient |
| | Caregivers | Patty Johnson |
| | Doses | Sun  Mon  Tues  Wed  Thurs  Fri  Sat<br>Fluoxetine 4tsp 22:03 |
| | Organization | GMU Supported Living Org 1 |
| | Updated At | May 05, 2021 21:59 |
| | Created At | May 05, 2021 21:59 |

Notification History   Devices

| Dose Time (UTC) | Medicine | Type | Scheduled | Sent |
|---|---|---|---|---|
| No Notifications found | | | | |

- 12 Mar — Good
- 11 Mar — Bad — Eating Increase
- 10 Mar — Good
- 9 Mar — Bad — Aggressive behavior
- 8 Mar — Bad — Irregular bowel movements
- 7 Mar — Bad — I can't see straight
- 6 Mar — Good Doses | Adherence Log | Impact Log

FIG. 8F

George Washington

- 8 Mar
  - Dose confirmed — Confirmed 50mg of Amoxicillin at 7:00 PM
  - Dose missed — Missed 50mg of Amoxicillin at 7:00 PM
- 7 Mar
  - Dose missed — Missed 1tsp of Azithromycin at 3:15 PM
  - Dose confirmed — Confirmed 1tsp of Azithromycin at 10:30 AM
  - Dose missed — Missed 10oz of Ibuprofen at 2:00 AM Doses | Adherence Log | Impact Log

TAMPER-RESISTANT CONTAINER WITH UNIQUE IDENTITY AUTHENTICATION AND NETWORK-ENABLED SECURITY FEATURES

CROSS-REFERENCE TO RELATED APPLICATIONS

The present application claims priority to and the benefit of U.S. patent application Ser. No. 16/923,641, filed Jul. 8, 2020, which in term claims priority to and the benefit of U.S. Provisional Application No. 62/871,425, filed Jul. 8, 2019, the contents of which is hereby incorporated by reference in its entirety.

STATEMENT REGARDING FEDERALLY SPONSORED RESEARCH OR DEVELOPMENT

The invention described herein was made without federal funding.

BACKGROUND OF THE INVENTION

The present invention relates to the technical fields of medicine, pharmacy and telehealth. More particularly, the embodiments of the present invention include improved means for the secure dispensing of medications leveraging a combination of specialized medication dispensers with modern software applications and network communications technologies. The dispensers described herein are tamper resistant, may require a unique identification to authenticate the identity of the user and enable mobile locking, unlocking and alarming that assimilates with text messaging and smartphone capabilities via software applications and application programming interfaces (API). The tamper-resistant containers may also be configured with audio, visual or vibratory alarms to alert users of unauthorized attempts to access the contents, as well as displays used as rewards for adherence to prescription dosing regimens.

Existing conventional medication dispensers lack mobile locking, unlocking and alarming capabilities, and are not accompanied with unique user identity authentication. Generally speaking, the patient or other user must open a childproof pill lid, for example, to gain access to the medication inside the bottle or case. With conventional pill bottles, the patient's medication is vulnerable to being stolen, moved, tampered with and not completely secured, and provides no mechanism to alert the patient or a patient custodian if tampering occurs. It is thus an object of the invention of the present disclosure to provide a secure, tamper-resistant container that leverages cloud computing and software application technologies to prevent unauthorized access to medications and alert users when attempts at such unauthorized access are made, as well as provide a mobile means of locking and unlocking containers of medicine. It is a further object of the invention to provide an interactive mobile software application for rewarding patients for prescription compliance with games, avatars and the like visible on a graphical user interface (GUI) to encourage patients suffering from autism or other similar disabilities, for example, affecting compliance to take the appropriate doses of necessary medications timely.

It is yet another object of the present invention to provide institutions such as nursing homes and the like with a system designed to improve patient adherence to single or multiple prescriptions and enable remote refilling as needed. It is another object of the invention to enable such institutions to receive updates from doctors' offices and pharmacies regarding changes to medication regimens for their residents. These and other benefits of the invention described herein will be evident to those of ordinary skill in the art in the applicable technical fields.

SUMMARY OF THE INVENTION

The present invention comprises tamper-resistant containers of resilient material that may include network enabled security features for improved medication security and adherence. In one aspect, containers according to the present invention are fabricated from durable plastic material and are configured to dispense multiple single dose packs or units contained in multi-unit blister packs. The latter may comprise punches for automated dispensing the pills contained in each blister pack. A container according to the present disclosure may also be configured with a power source, such as a rechargeable battery with a universal serial bus (USB) port, that powers a unique user identity authentication sensor, such as but not limited to a fingerprint biometric scanner, in combination with a vibration sensor to detect container movement. The user identity authentication and vibration sensors may communicate via Bluetooth transceiver to a smartphone or via an available wireless network to a cloud server comprising software program instructions which when executed by a processor cause the processor to process the data inputs for authentication or transmit alerts to untimely or unauthorized access to a smartphone configured to receive messages on a GUI or via short message service (SMS) text in communication with the cloud server via wireless network.

For example, and not by way of limitation, a smartphone may receive text messages and audio, visual or vibratory alerts, and may be configured to enable authenticated, remote locking or unlocking of an associated container. A system of the present disclosure may also enable updates and reminders to be sent to a smartphone regarding dosing times, the need for refills, and changes to dosing regimens. These features provide the following benefits: (1) instantly alerting of parents, friends or loved ones of unauthorized users attempting to steal pills; (2) simplification of the outdated methods of opening pill bottles and cases through access only upon authentication, such as by fingerprint reading or another suitable authentication means; and (3) eliminating unauthorized users from breaking into or cutting open pill bottles or cases to steal pills by using tough, durable manufacturing material.

The secure dispensers of the present disclosure may integrate with smartphones via an API installed thereon, which enables text messaging to provide users with an easy to use link for live updates and locking and unlocking of the system. In addition, users benefit from modern mobile application capabilities that provide real-time awareness and access to medication data for individuals, their guardians, or healthcare providers. An application according to the present disclosure may also provide for data collection and logging to gain insights into historical performance of the dispensers and adherence to prescriptions. Gamified education and training is also enabled to assist patients with various disabilities with medication compliance. The mobile application functionalities may also be enabled in the form of a web application accessible via an Internet website provided by the applicant or third party. These and other benefits of the invention of the present invention will be apparent to one of ordinary skill in the art in view of the disclosure that follows.

BRIEF DESCRIPTION OF THE DRAWINGS

FIGS. 7A-7C illustrate screenshots from a web application as described herein.

FIGS. 8A-8F illustrate first set of screenshots from a smartphone configured with a mobile application as described herein.

DETAILED DESCRIPTION OF THE INVENTION

The invention of the present disclosure comprises a durable, secure, medication dispenser, which may be used in connection with a provided software application which can run on a web server or be downloaded to a mobile device such as a smartphone or tablet and be utilized by authenticated users to dispense and refill medications, or be used to provide rewards to individual patients for medication compliance. It is an object of the present invention to ease access to medications and prescription compliance, and to reward compliance with video games and graphics viewable on a smartphone, for example. It is another object of the invention to permit only authorized access to medications contained in the dispenser, alert users of a system as described herein to unauthorized or unscheduled attempts to dispense medications therefrom, and improve compliance with prescription dosing regimens, particularly in cases where the individuals to whom the medications are prescribed have some form of difficulty adhering to prescription schedules.

Figure 1:
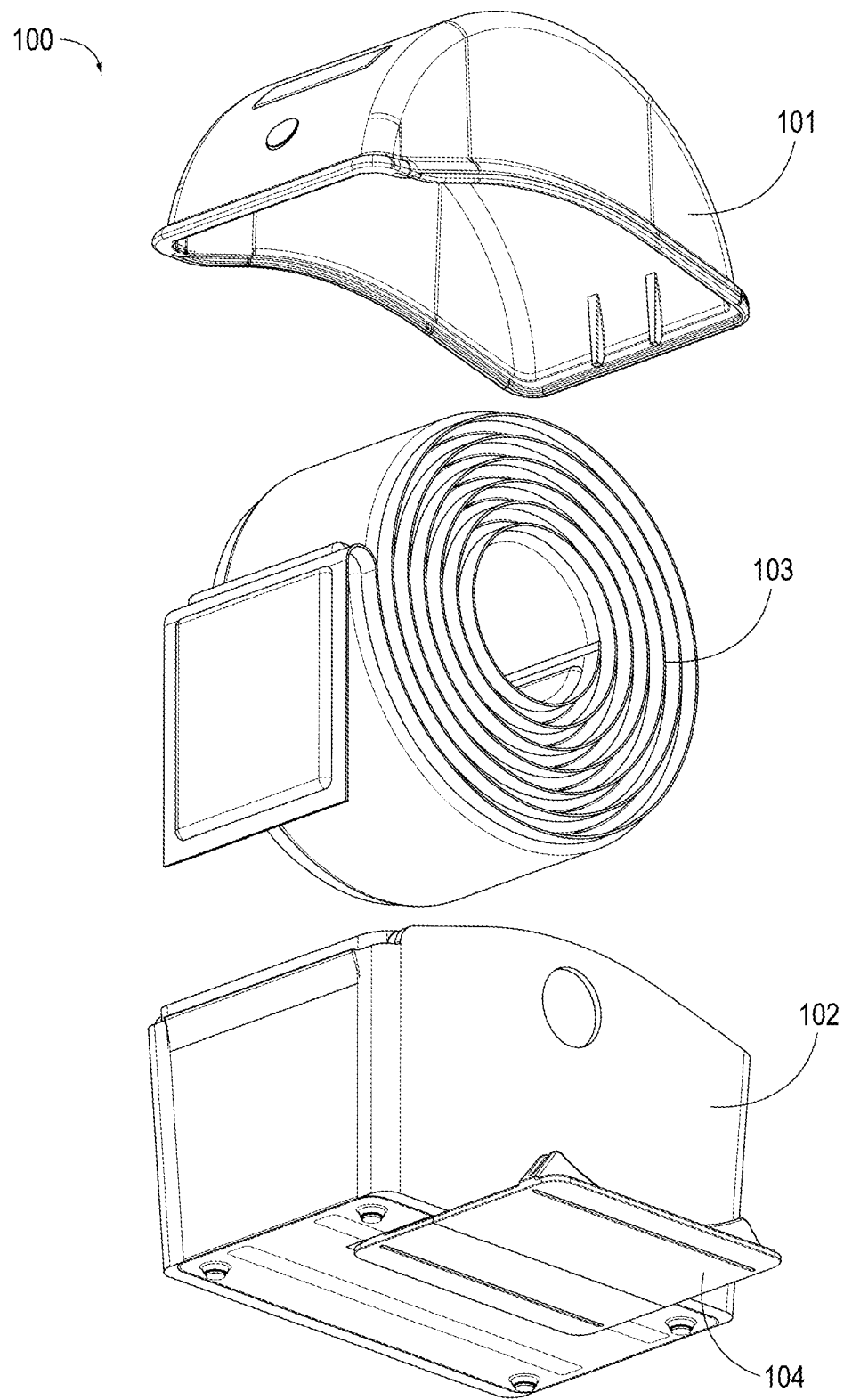
FIG. 1 is an exploded view of an exemplary embodiment of a medication dispenser according to the present disclosure.
Figure 2:
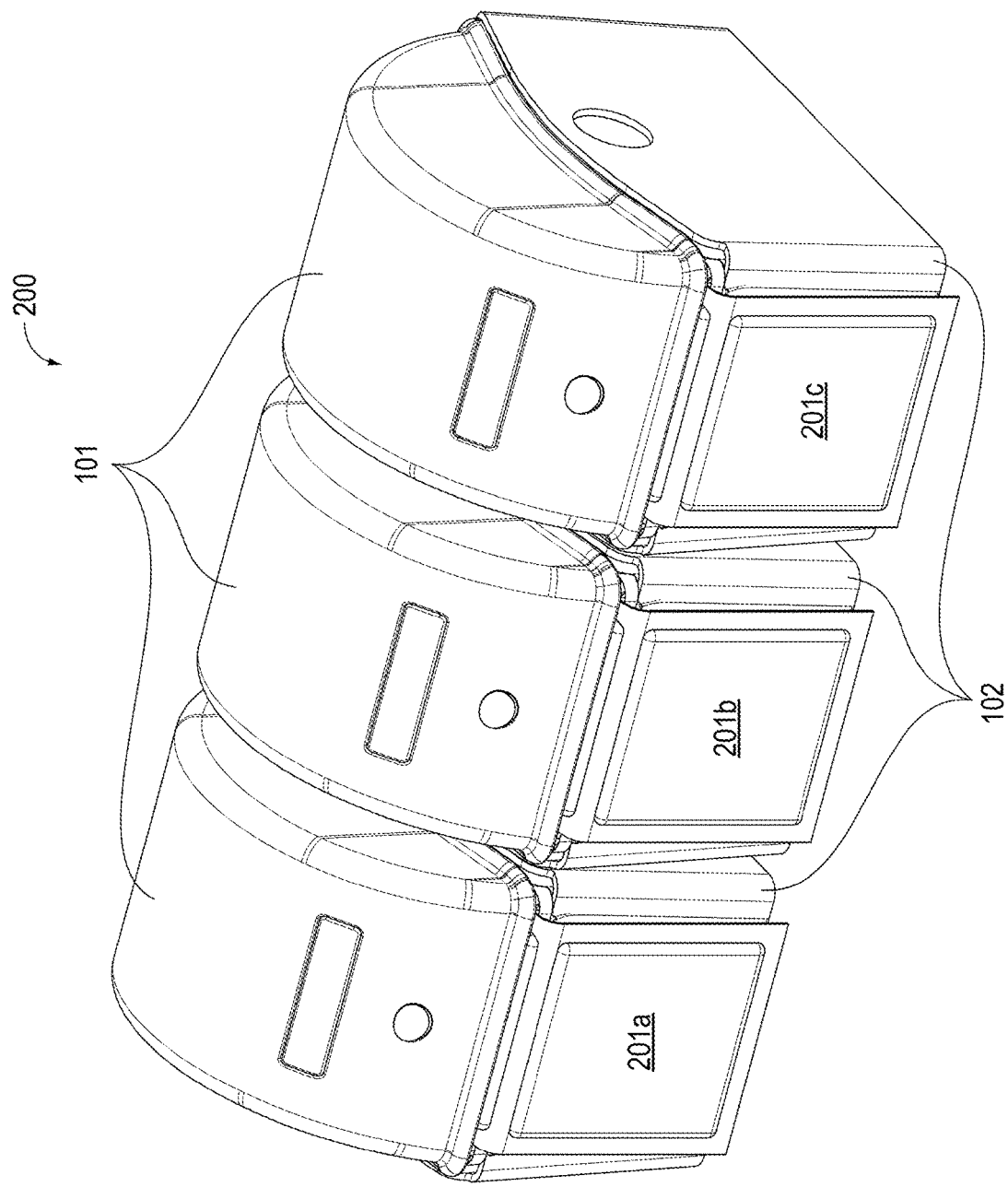
FIG. 2 illustrates multiple connected units as illustrated in FIG. 1 with lids closed.

The invention of the present disclosure will be best understood with reference to the accompanying drawings. FIG. 1, for example, illustrates an embodiment of a container according to the present invention configured for dispensing of single packets, each containing one or more medications, of a connected series of packets. This illustrative embodiment 100 comprises a lid 101 that fits securely over a container 102, the lid 101 and container 102 being fabricated of durable material and of suitable size to contain a roll 103 of individual medication packets that may be dispensed one at a time. Each unit as shown in FIG. 1 may be equipped with a base connector 104 to enable connection of a series of units 200, as illustrated in FIG. 2, each containing a roll 103 of a different medication, for example.

In the case of institutional use, each unit may be loaded with medications for a different patient and configured with network-enabled security features for automated dispensing in response to instructions provided by a user of a software application as described herein. Alternatively, an individual may self-dispense in response to an alert to take a dose of medication, and dispensing may trigger a reward in the form of a game or graphic display visible on a smartphone of the individual taking the medication. Individual packets 201a, 201b and 201c may be dispensed at the discretion of an individual or administrator.

Figure 3A:
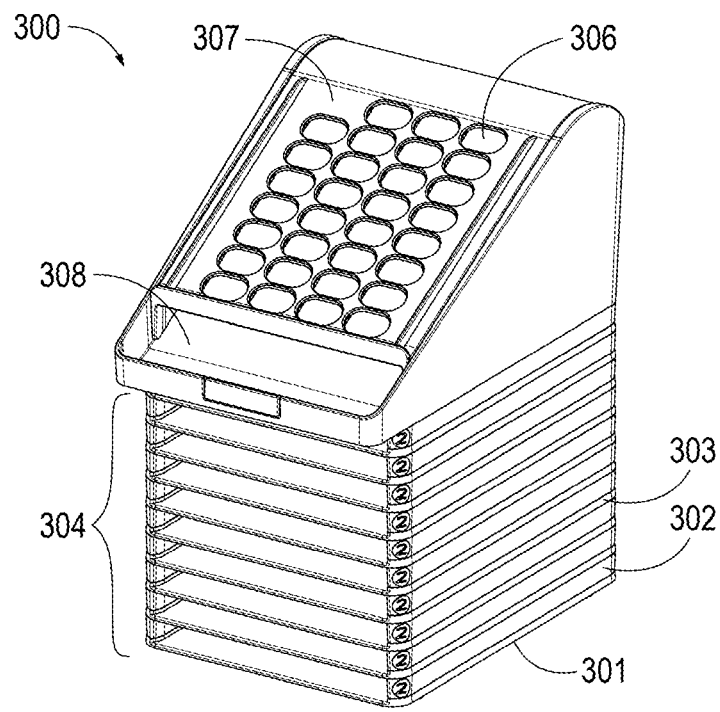
FIG. 3A is an upper perspective view of a blister pack dispenser according to an embodiment of the present disclosure.
Figure 3B:
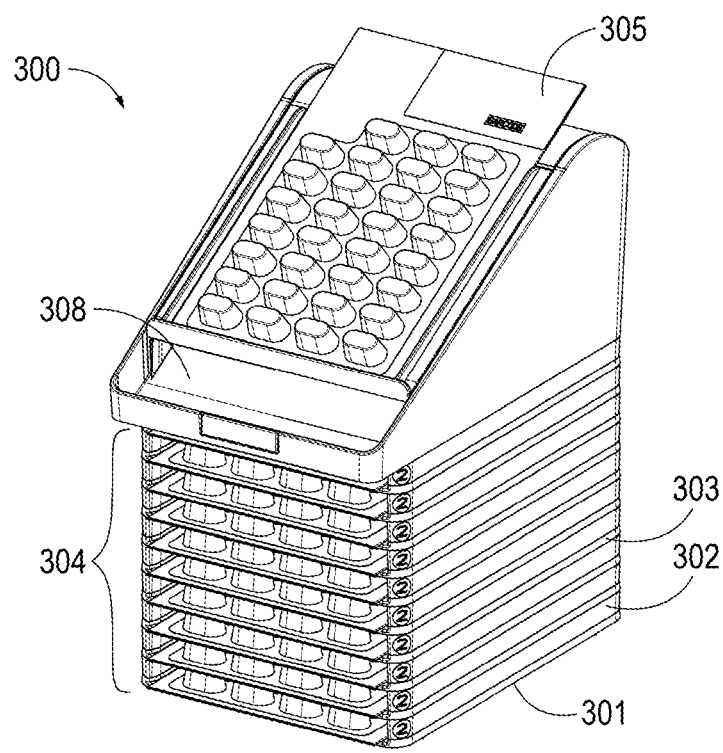
FIG. 3B is an upper perspective view of a container as illustrated in FIG. 3A, with blister packs loaded.

An exemplary dispenser 300 according to the present disclosure may be configured to accommodate several blister packs containing several doses of medication (e.g., pills or capsules), as illustrated in FIGS. 3A (empty) and 3B (loaded). As shown in FIGS. 3A and 3B, a base tray 301 and a plurality of spacers 302 and upper trays 303 may be connected to create a magazine 304 containing multiple blister packs for manual distribution by pushing each pill or capsule through an opening 306 in a top tray 307 configured with a plurality of openings of suitable size and shape to accommodate a corresponding blister pack 305. A receiving tray 308 may be provided to receive a dispensed medication when pushed through an opening 306. As is the case with the design illustrated in FIG. 1, base connectors may be provided so multiple dispensing units according to FIGS. 3A and 3B may be connected, each used to house individual prescription medications for individuals requiring multiple medications, or in the case of institutional use, individual medications for different patients, in order to prevent confusing the prescriptions for one another.

Figure 4:
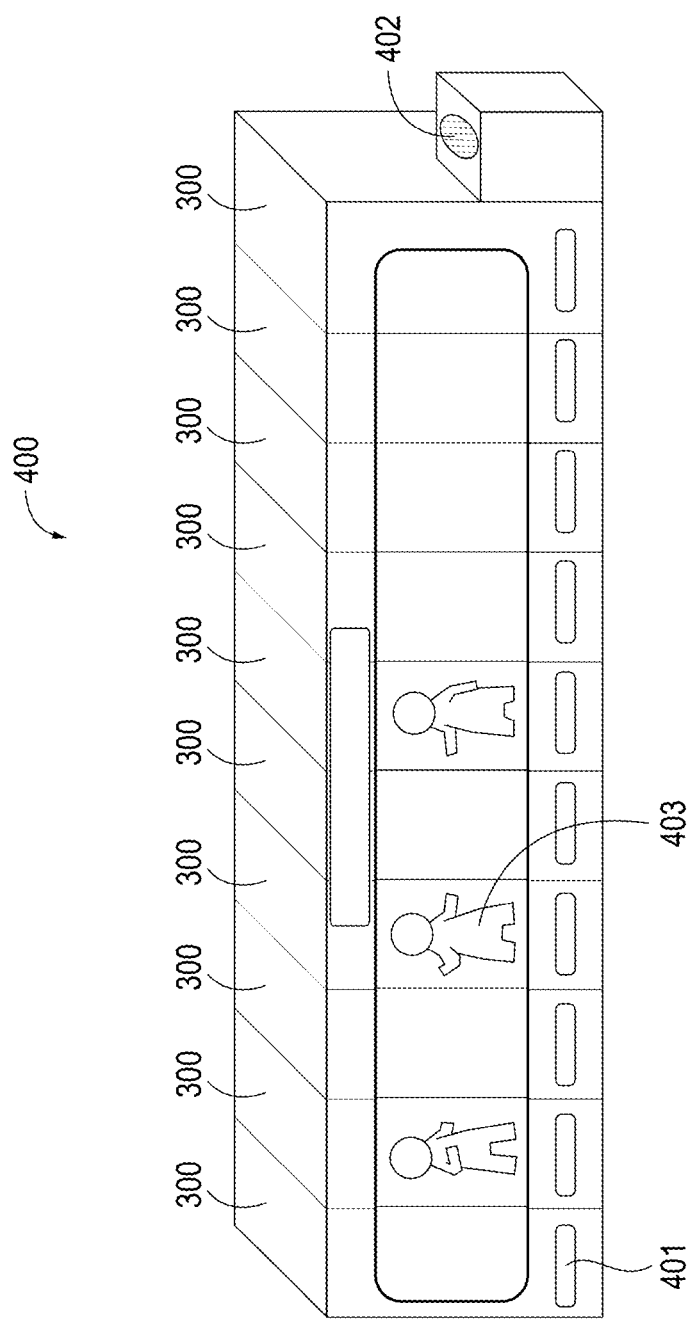
FIG. 4 illustrates a connected series of closed containers according to the present disclosure, including avatar displays on some units and a fingerprint scanner for secure access.

Each unit according to FIGS. 3A and 3B may be secured by providing a cover of durable material that fits over the entire unit, as illustrated in FIG. 4. In this way, multiple units 300 may be connected in series 400 and secured. Continuing with FIG. 4, an authentication means such as a fingerprint scanner 402 may be provided, along with LED lighting and screens on which graphics may be displayed as rewards for timely dispensing of medications in response to instructions provided using a connected mobile application after authentication. Each cover shown in FIG. 4 is configured with a slot 401 though which medications may be dispensed by gravity after authorization. For prescription compliance training for individuals suffering from difficulties in determining which medications to take and when, adherence may be gamified and rewards such as the display of avatars 403 as illustrated in FIG. 4 may be provided as an additional feature of the present invention.

Figure 5:
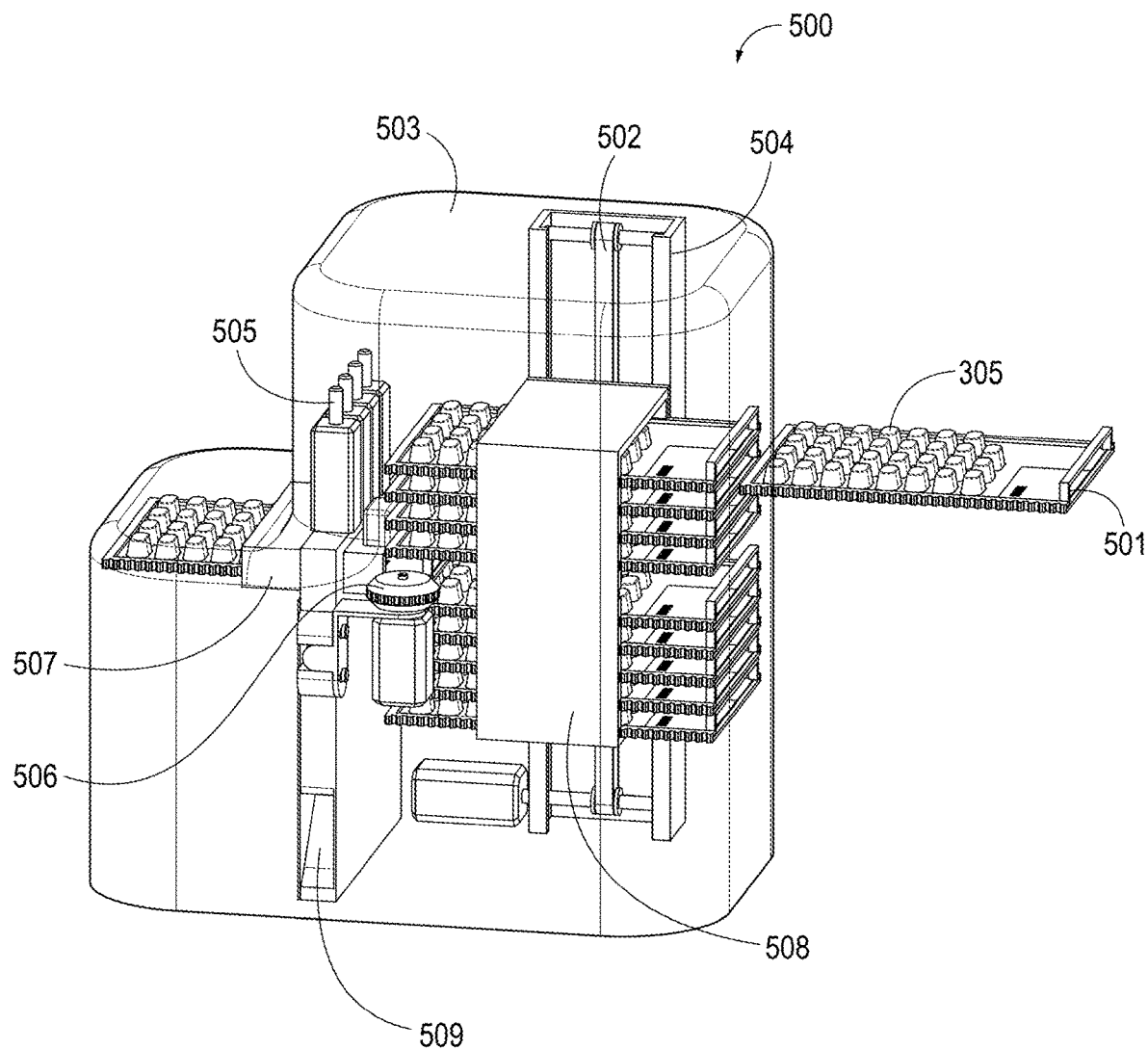
FIG. 5 illustrates a secure blister pack dispenser according to an embodiment of the present disclosure, configured for automated dispensing of medications.

Certain embodiments of a container according to the present disclosure may be configured with various mechanical parts to enable automated dispensing of dosing regimens comprising a plurality of blister packs as shown in FIG. 5. In this illustrative embodiment 500, a secure housing 503 contains a magazine, in turn containing a blister pack trays 501, similar to those described with reference to FIGS. 3A and 3B, is held within a sliding bracket 508 secured to a vertical conveyor 502 of a conveyor tower 504 for mechanical raising and lowering in response to instructions provided by a connected software application to dispense appropriate medications. The unit illustrated in FIG. 5 500 is configured with a row of punches 505 corresponding to the locations of blisters within each row and column within a blister pack 305. The unit of FIG. 5 500 is configured with a conveyor (not shown) that moves each blister pack tray 501 forward toward the punches 505 in order to line the medications up via tray guide 507 with the punches as needed, then each punch can be selected for activation and push the medication contained in the assigned blister out of the pack and into a chute 509 where it is gravity-dispensed.

In certain embodiments, a plurality of punches 505 may be provided to punch the required blister for the designated time and date of a dose of a medication contained therein. Magazine cartridge options may include but are not limited to 5, 10, 15 and 20 single blister pack magazine cartridges configured for vertical movement. Individual blister pack cartridges 501 may include horizontal gears 506 with motion controls to place the medication in the blister pack in the correct position for punching. Gravity dispensing of individual medication units from the punched blister pack to a chute 509 below may be employed. A spring loaded gear pass through control may also be provided. Radio frequency identification (RFID) sensors may be employed in order to collect medication data, or alternative means may be used as will be familiar to one of ordinary skill in the art, from the blister packs 305 to ensure proper medication selection. Individual units may be provided in series to better serve the needs of those requiring multiple medications.

A web or mobile application according to the present disclosure may be configured for use either by the individual to whom medications have been prescribed, or by caregivers, including parents, guardians, or institutional caregivers such as nursing staff and doctors. The user interfaces for each type of user are differentiated for customized, appropriate user experiences.

Figure 6:
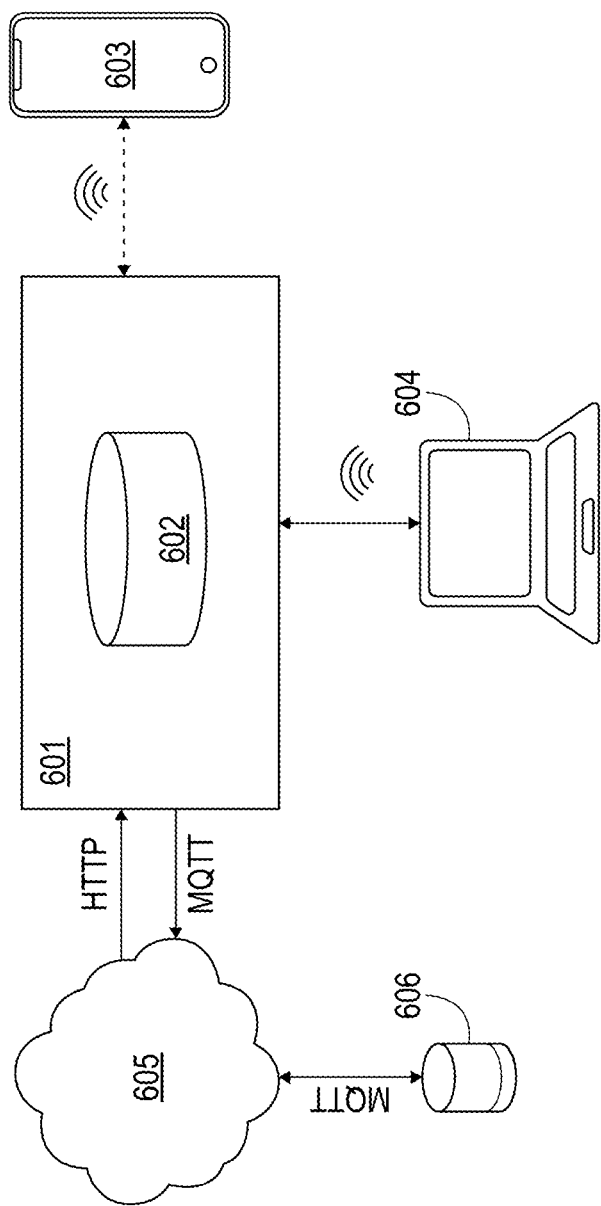
FIG. 6 illustrates an exemplary system architecture for enabling certain container features described herein and the claimed methods.

The invention of the present disclosure is supported by a backend system comprising components such as those illustrated in FIG. 6. In this exemplary embodiment, a web server 601 in network communication with a cloud server 605 via Hypertext Transfer Protocol (HTTP) (incoming) and Message Queuing Telemetry Transport (MQTT) protocol (outgoing), the cloud server 605 being in wireless communication with a tamper-resistant container according to the present disclosure via MQTT, supports system functionality. A smartphone 603, for example, configured with an API for interaction with a computer software application tangibly stored on a non-transitory computer readable medium, support functionality of a mobile application as described herein. For mobile applications, a cloud server 605 may support the running of the application. Data inputs from a smartphone 603 (or computer via website) are processed according to the instructions contained in the software application by a microprocessor in network communication with a cloud server 605, for example. Processing includes but is not limited to user authentication, locking or unlocking of a medication dispenser, or alerting or messaging the smartphone 603. The system is designed to anonymize all data traffic to and from a container as described herein, thereby maintaining the data privacy of individual users of a system comprising a container as described herein. Data collected and stored within a system of the present disclosure may be stored on a database 602 and related to the utilization of a container as described herein to enable analytics for users. Updates can be pushed out by an administrator to the web server 601 using any suitable computing means 604.

Users of a system as described herein determine who should have access to the system and set permissions according to their role as user, custodian, physician, etc. Users may input information on medications, dosages, dosage regimens and so forth to better manage adherence to prescription requirements. In preferred embodiments, a container according to the present invention may hold up to four weeks of medication schedule to be dispensed up to four times per day, although this is by way of example and not limitation. A system of the present disclosure may be configured to interface with pharmacies through telehealth programs to enable seamless refilling and delivering of medications prior to running out.

In certain embodiments, a system of the present invention also may provide guided medication adherence instructions for custodians or individuals taking medications. These may be communicated via audiovisual means over a computing means such as a smartphone. It is an object of the present invention to teach better medication adherence to individuals who suffer from intellectual developmental disabilities (IDD) such as Autism Spectrum Disorder (ASD) or attention deficit disorder who may have difficulty focusing on proper adherence.

Specific embodiments of the present invention comprise a tamper resistant pill dispenser with unique identity authentication and mobile locking, unlocking and alarming capability, integrated into a system comprising a computer software application accessible via a smartphone or physically located on the dispenser. Future enhancements may be made based on system testing along with user input and feedback.

It is an object of the present invention to provide alerts, enable remote locking and unlocking, and communicate updates and reminders related to medication schedules, refill needs and the like. It is also an object of the invention of the present disclosure to enable the authenticated user to access medications contained inside the container only following authentication such as by fingerprint scanning. While a medication dispenser according to the present disclosure may be made of stainless steel, aluminum, or of any other sufficiently rigid and strong material such as high-strength plastic, metal, composites and the like, the various components of the dispenser can be made of different materials. A dispenser may also be configured with a Bluetooth transceiver for short wave transmission of data to a smartphone or the like in wireless network communication with a cloud server in further communication with a web server comprising a software application tangibly stored thereon which supplies instructions which when executed by a processor cause the processor to process data from the dispenser, such as but not limited to vibration, motion or authentication data.

As explained briefly throughout the preceding disclosure, a system according to the present disclosure may be accessible in the form of a web application available over the Internet on a website, or a mobile application downloadable to a compatible device. As shown in FIGS. 7A-7C, a web application is designed to provide a top-down view for administrators to view all individual associated patients benefitting from the system. For example, a long-term care agency administrator may include all caregivers and other staff associated with medication management at his or her institution for access, as illustrated in FIG. 7A. Data visualizations and data analytics may be included on a dynamic dashboard providing a single site for key performance indicators (KPIs) to be displayed to web application users. Users may create various profiles according to known practices in the art, with administrators having the ability to create, edit and delete users within their organizations and all necessary fields for use of the system, including personal information, prescription information, and so on. Where the user of the system is an individual, self-administration may be desired.

As shown in FIG. 7B, an administrator may populate all the necessary fields appropriate for medication management for a given individual within an institution, for example. Turning to FIG. 7C, fields so populated are illustrated. A system of the present disclosure provides an interface to input medication regimen data. Users can input full medication regimens for individuals, such as schedule (day, time, and frequency per day of dosing), medication type, dose amount, expiration date, refill date, etc. Pharmacy software integrations may be used to automate the otherwise manual entry of this data. A system according to the present disclosure may enable a feedback loop between pharmacies and long-term care agencies for real-time changes, such as when a medication change occurs (the pharmacy can update the regimen and update the system entries). In preferred embodiments, a web application of the present disclosure will also allow for data export based on different views, such as, for example, exporting a medication compliance history to share with medical professionals using compatible file types.

Figure 8B:
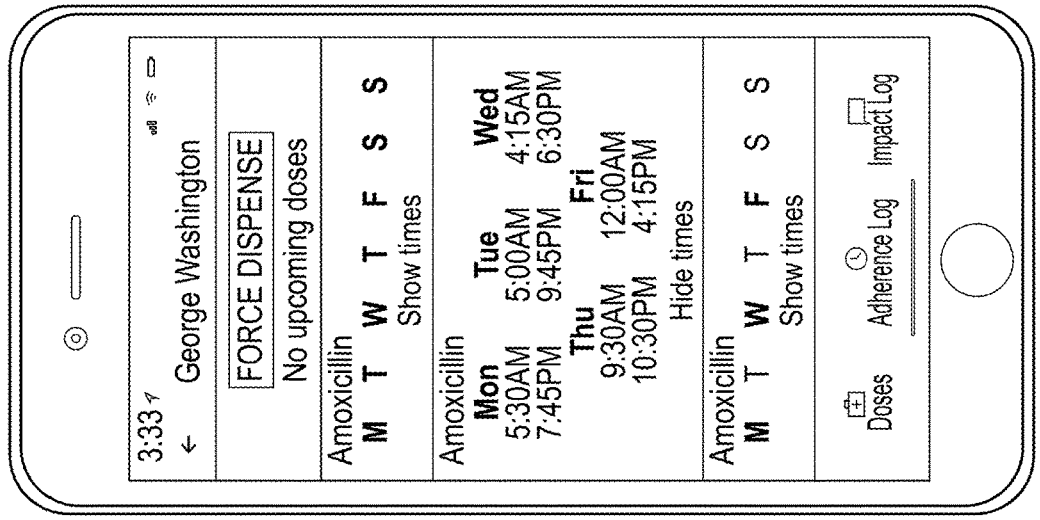
Figure 8A:
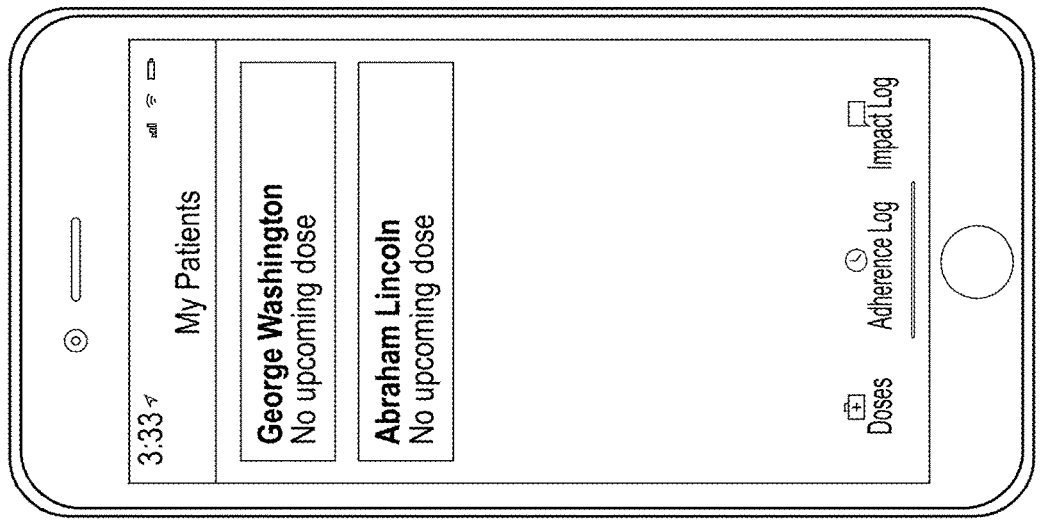
Figure 8D:
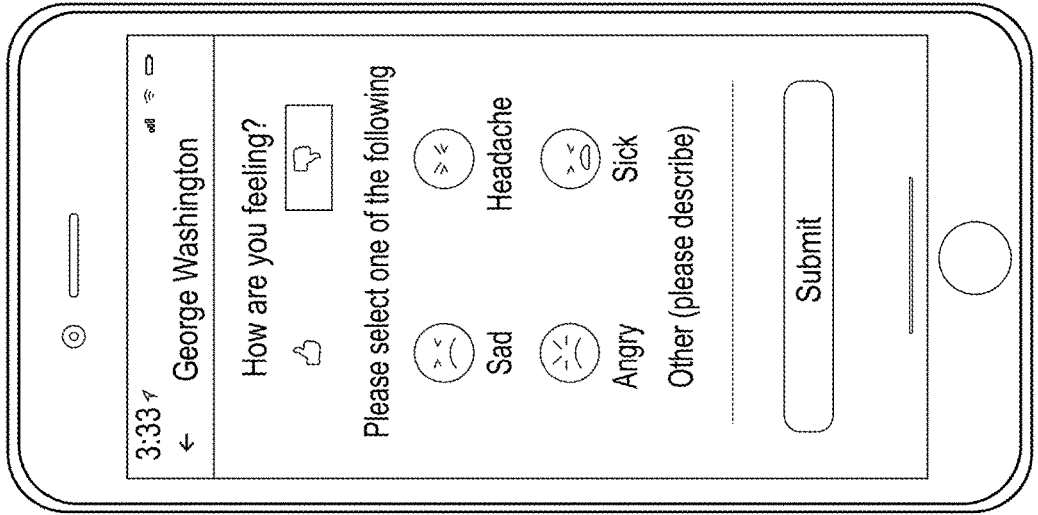
Figure 8C:
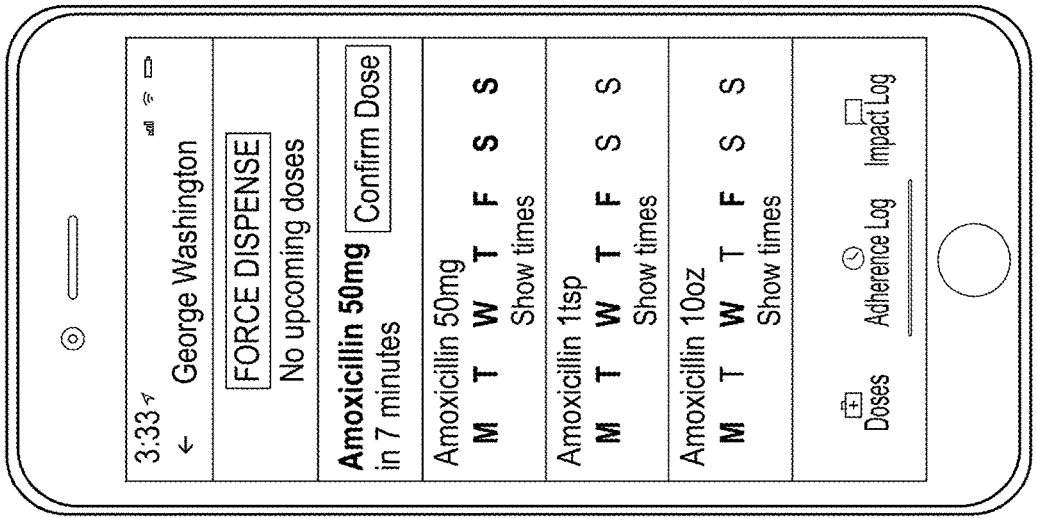

Turning now to a mobile application as contemplated herein, the app is designed to provide real-time awareness and access to medication data to individuals and their supporting personnel. Exemplary mobile screen views are illustrated in FIGS. 8A-8F. FIG. 8A names the patients associated with an administrator following secure login. In FIG. 8B, after selecting a patient that patient's full medication schedule becomes visible. From there, the administrator can force dispense the confirmed dosage and ensure it is correct as shown in FIG. 8C.

Reminders are provided when medications are due to be taken or administered, as well as when they expire or when refills are due. Alerts may be pushed to a user device if doses are missed or dispensed late, or if potential threats are detected, such as theft or overdose attempts. Data collection and logging for insights into historical performance may also be featured. For example, medication impact logging functionality may push a notification to a user asking how they are feeling then provide custom interfaces familiar to users where they can input data to describe how they are feeling and uncover reactions such as potential medication side effects, as illustrated in FIGS. 8D-8F.

Full historical logs of medication compliance for individuals are enabled by a system according to the present disclosure. A caregiver may be able to view logs for all associated individuals. Full historical logs of medication impacts driven by input taken from individuals as well as caregivers is possible.

A system of the present disclosure also provides gamified education and training for individuals having difficulty with medication adherence. Routine, repetition, and rewards-based experiences for individuals and caregivers are used to motivate users to comply with medications, understand the impacts of complying, and drive independence. Upon setup, users may be taken through a set of interactive surveys to understand their interests and behaviors, to be later introduced in the user experience. For example, a user may select types of games that he or she enjoys, and may unlock these types of games as they become more independent and advance through training modules. Using yet another example, a user may select types of characters they enjoy viewing, and an avatar may be generated for that individual to guide through training and education modules.

Preferred embodiments of mobile applications will allow users (depending on authorization settings) to interact with their devices. Examples of interactions include dispensing medications (e.g., user pressing a button in the app that makes the device dispense the correct dose at that time). Once medications are loaded, accessed, and dispensed from the device these steps in the process will be made relevant in the mobile app interface to provide the users with various insights over time. Regulatory automation may also be enabled by a system as described herein, with on object of automating the three-way check currently required at long-term care agencies. Rather than comparing a scanned copy of physical form of identification, for example, methods employed by the mobile app may include facial recognition to validate the identity of an individual. Rather than comparing the label on a doctor's order to the label on a medication, integrated pharmacy software may validate using the code which exists on the medication packaging currently stored in the device. Rather than remembering to look up medication administration instructions and preferences form a multitude of physical forms, a reminder may be sent to the medication administrator (caregiver) or the individual depending on permissions with a description.

The advantages of the systems and methods described herein include, without limitation, significant reduction in the ability to tamper with or break into the container and steal controlled substances or illegally access prescription medication, automatic notification to the owner if a break-in attempt occurs, simplicity of access for the content owner, and accessibility and data tracking via a computer software application, preferably accessible from a mobile computing device. Future enhancements over the current state of the art include, but are not limited to the use of a fingerprint scanner, for example, which may already be accessible by mobile phones and the like; integration of video, audio, camera and global positioning system (GPS) functions; automatic transmission of reminders when to take medication and warnings on side effects; and integration with Internet of Things (IoT) type devices; live results from wearable health monitors and sensors; alerts of drug interactions and lockout periods based on instructions for administration; and interfaces with available pharmaceutical prescription information, dispensing guidelines and directions of when to take the medication. The final shape, size, weight and dimensions of the invention may be customized through developmental, operational and user testing.

While the foregoing written description of the invention enables one of ordinary skill to make and use what is considered presently to be the best mode thereof, those of ordinary skill in the art will understand and appreciate the existence of variations, combinations, and equivalents of the specific embodiments, methods, and examples described herein. The invention should therefore not be considered limited according to the illustrative embodiments described herein, but by all embodiments and methods within the scope and spirit of the invention as claimed.

What is claimed:

1. A medication storage and access system, the system comprising:
    a plurality of modular containers of durable material and a locking mechanism configured to secure medication packaging within each of the plurality of containers and allow for individual units to be accessed via the software application to allow for individual doses of a prescribed medication to be detached manually;
    a base configured to connect each of the plurality of containers; and
    a portable electronic device comprising a mobile software application in network communication with a software module tangibly stored on a non-transitory computer readable medium, the software module further comprising instructions which when executed by a processor cause the processor to:
        alert a user of the portable electronic device of the need to take the prescribed medication;

display a confirmation button on a graphical user interface (GUI) of the portable electronic device; and when the button is pushed, display a reward on the GUI selected from the group consisting of graphics, videos or games;

wherein the plurality of containers are in network communication with the software module and the reward is displayed automatically when the prescribed medication is detached.

2. The system according to claim 1, wherein the base connector is configured to fasten to the bottom of each container and the next in a row of systems.

3. The system of claim 1, wherein the medication packaging is any one of a single-dose blister card, a multi-dose blister card, a single-dose strip pack, a multi-dose strip pack, a pill bottle, a liquid medication bottle, a topical container, and an injection package.

* * * * *